United States Patent [19]

Miller et al.

[11] 4,199,591
[45] Apr. 22, 1980

[54] DIELS-ALDER ADDUCTS OF 3-ISOTHIAZOLONE 1-OXIDES AND 1,1-DIOXIDES

[75] Inventors: George A. Miller, Maple Glen; Ernest D. Weiler, Ambler, both of Pa.

[73] Assignee: Rohm and Haas Company, Philadelphia, Pa.

[21] Appl. No.: 11,291

[22] Filed: Feb. 12, 1979

Related U.S. Application Data

[62] Division of Ser. No. 642,423, Dec. 19, 1975, abandoned.

[51] Int. Cl.$^2$ .................... C07D 275/06; A01N 9/12
[52] U.S. Cl. .................................... 424/270; 71/67; 548/210; 548/209
[58] Field of Search ............................ 260/301, 302 F; 424/270

[56] References Cited

U.S. PATENT DOCUMENTS

| | | | |
|---|---|---|---|
| 2,892,835 | 6/1959 | de Stevens | 260/302 F |
| 3,197,472 | 7/1965 | Vest | 260/302 F |

*Primary Examiner*—Alton D. Rollins
*Assistant Examiner*—Lisa Jones

[57] ABSTRACT

The preparation and use of Diels-Alder adducts of 3-isothiazolone 1-oxides and 1,1-dioxides are disclosed. These compounds and compositions containing them are useful in controlling weeds and microorganisms such as algae, bacteria, fungi and the like.

9 Claims, No Drawings

DIELS-ALDER ADDUCTS OF 3-ISOTHIAZOLONE 1-OXIDES AND 1,1-DIOXIDES

This is a division of application Ser. No. 642,423 filed 12/19/75 now abandoned.

This invention relates to certain novel Diels-Alder adducts of 3-isothiazolone 1-oxides and 1,1-dioxides, to compositions containing them and to their utilization in the control of weeds and microorganisms such as bacteria, fungi, algae and the like.

A further embodiment of this invention is the discovery that 3-isothiazolone-1 oxides and 1,1-dioxides are dienophiles and can undergo Diels-Alder reactions with any compounds possessing reactive conjugated double bonds and that certain of these compounds possess herbicidal and microbicidal activity.

The novel compounds of this invention are represented by the formula:

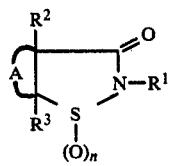
(I)

wherein $R^1$ is a hydrogen atom; an alkyl group, preferably having 1 to 18 carbon atoms, most preferably 1 to 8 carbon atoms; a cycloalkyl group preferably having 3 to 12 carbon atoms; an aralkyl group, preferably having up to 11 carbons, most preferably benzyl or phenethyl; an aryl group preferably having up to 10 carbon atoms most preferably phenyl; $R^2$ and $R^3$ are independently a hydrogen atom, a halogen atom or an alkyl group of from 1 to 4 carbon atoms, most preferably a hydrogen atom, a halogen atom or a methyl group; n is the integer 1 or 2; and A is a group of the formula

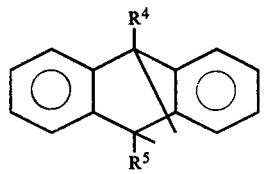
(II)

wherein $R^4$ and $R^5$ are independently a hydrogen atom, a halogen atom or a ($C_1$-$C_4$) alkyl group; or A is a group of the formula

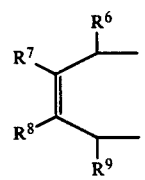
(III)

wherein $R^6$, $R^7$, $R^8$ and $R^9$ are independently a hydrogen atom, a halogen atom or a ($C_1$-$C_4$) alkyl group; or A is a group of the formula

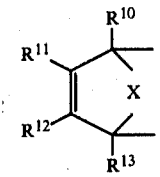
(IV)

wherein $R^{10}$, $R^{11}$, $R^{12}$ and $R^{13}$ are independently a hydrogen atom, a halogen atom, or a ($C_1$-$C_4$) alkyl group; and X is oxygen, sulfur or the group $$-(CY_2)_p-$$ (V)

wherein Y is a hydrogen atom or a halogen atom and p is the integer 1 to 2.

The term "alkyl" as used in the specification and claims is meant to include branched or straight chained aliphatic hydrocarbons of up to 18 carbon atoms except where indicated otherwise, which can be unsubstituted or substituted with up to three substituents, preferably one substituent such as hydroxyl, halogen, ($C_1$-$C_4$) alkoxy, cyano, carboxy and the like.

The term "aralkyl" as used in the specification and claims is meant to include aralkyl groups of up to 11 carbon atoms which can be unsubstituted or substituted with up to two substituents such as halogen, ($C_1$-$C_4$) alkyl, ($C_1$-$C_4$) alkoxy, nitro, cyano, trihalomethyl and the like.

The term "aryl" as used in the specification and claims is meant to include phenyl or naphthyl groups which can be unsubstituted or substituted with up to two substituents such as halogen, ($C_1$-$C_4$) alkyl, ($C_1$-$C_4$) alkoxy, nitro, cyano, trihalomethyl and the like.

The preferred compounds of this invention certain of which exhibit herbicidal and/or microbicidal activity are those of Formula (I) wherein $R^1$ is a hydrogen atom or an alkyl group preferably having 1 to 18 carbon atoms, most preferably 1 to 8 carbon atoms; $R^2$ and $R^3$ are independently a hydrogen atom or a halogen atom, preferably a hydrogen atom or a chlorine atom; n is the integer 1 or 2; and A is a group of Formula (II) wherein $R^4$ and $R^5$ are independently a hydrogen atom or a methyl group; or a group of Formula (III) wherein $R^6$, $R^7$, $R^8$ and $R^9$ are independently a hydrogen atom or a methyl group; or a group of Formula (IV) wherein $R^{10}$, $R^{11}$, $R^{12}$ and $R^{13}$ are independently a hydrogen atom, a halogen atom, preferably a chlorine atom or a methyl group; and X is the group of Formula (V) wherein Y is a hydrogen atom or a chlorine atom and p is the integer 1 or 2.

The most preferred compounds of this invention certain of which exhibit postemergence herbicidal and/or fungicidal activity are those of Formula (I) wherein $R^1$ is a hydrogen atom or an alkyl group of from 1 to 8 carbon atoms; $R^2$ and $R^3$ are hydrogen atoms; n is the integer 1 or 2; and A is a group of Formula (II) wherein $R^4$ and $R^5$ are hydrogen atoms; or a group of Formula (III) wherein $R^6$, $R^7$, $R^8$ and $R^9$ are hydrogen atoms; or a group of Formula (IV) wherein $R^{10}$, $R^{11}$, $R^{12}$ and $R^{13}$ are hydrogen atoms or chlorine atoms; and X is the group of Formula (V) wherein Y is a hydrogen atom or a chlorine atom and p is the integer 1 or 2.

Typical compounds encompassed by the scope of this invention are:

3a,4,7,7a-tetrahydro-2,4,5,6,7-pentamethyl-1,2-benzisothiazol-3(2H)-one 1-oxide 2-decyl-3a,4,7,7a-tetrahydro-4,4,7,7-tetramethyl-1,2-benzisothiazol-3(2H)-one 1,1-dioxide 3a,4,4,7,7,7a-hexachloro-2-octadecyl-1,2-benzisothiazol-3(2H)-one 1-oxide 5,6-dibutyl-3a,4,7,7a-tetrahydro-2-octyl-1,2-benzisothiazol-3-(2H)-one 1,1-dioxide 2-cyclohexyl-3a,7a-difluoro-4,7dihydro-5,6-dimethyl-1,2-benzisothiazol-3(2H)-one 1-oxide 2-butyl-8,8,9,9-tetrachloro-3a,4,7,7a-tetrahydro-5,6-dipropyl-4,7-ethano-1,2-benzisothiazol-3(2H)-one 1,1-dioxide 2-(1,1-dimethylethyl)-4,7-dihydro-3a,7a-dimethyl-4,7-epoxy-1,2-benzisothiazol-3(2H)-one 1-oxide 3a,7a-dichloro-4,7-dihydro-2-octyl-4,7-epithio-1,2-benzisothiazol-3(2H)-one 1,1-dioxide 8,8-dibromo-2-hexyl-4,7-dihydro-3a,7a-dimethyl-4,7-methano-1,2-benzisothiazol-3(2H)-one 1-oxide 2-butyl-8,8-difluoro-3a,4,7,7a-tetrahydro-4,7-methano-1,2-benzisothiazol-3(2H)-one 1,1-dioxide 3a,7a-dihydro-4,5,6,7-tetramethyl-2-octadecyl-4,7-ethano-1,2-benzisothiazol-3(2H)-one 1-oxide 3a,4,7,7a-tetrahydro-5,6,-bis(1-methylpropyl)-2-tetradecyl-4,7-methano-1,2-benzisothiazol-3(2H)-one 1,1-dioxide 11,15-dichloro-9-methyl-13-octadecyl-14-oxo-9,10[4',5']-isothiazoloanthracene 12-oxide 11,15-dibromo-9-fluoro-13-octyl-14-oxo-9,10[4',5']-isothiazoloanthracene 12,12-dioxide 9,10-diethyl-11,15-difluoro-13-octyl-14oxo-9,10[4',5']-isothiazoloanthracene 12-oxide 13-dodecyl-9,10diiodo-11,15-dimethyl-14-oxo-9,10[4',5']-isothiazoloanthracene 12,12-dioxide 9,11-dibutyl-13-heptyl-14-oxo-9,10[4',5']isothiazoloanthracene 12-oxide The substituted 3-isothiazolone starting materials of the formula

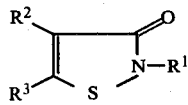

(VI)

can be prepared by methods described in U.S. Pat. Nos. 3,523,121 and 3,761,488 of Lewis et al. granted Aug. 4, 1970 and Sept. 25, 1973, respectively, and U.S. Ser. No. 855,046, filed Sept. 3, 1969 by Lewis et al. and now abandoned, all of which are herein incorporated by reference. The 3-isothiazolones in which $R^2$ is a methyl group can also be prepared by the cyclization of a dithiodiisobutyramide of the formula

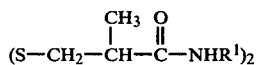

(VII)

wherein $R^1$ is as defined above. The cyclization is generally carried out by the simultaneous addition of a halogenating agent and an amide, to a solvent, such as ethyl acetate, dimethylformamide, acetone or the like. The cyclization reaction is preferably carried out at a temperature from about 25° to about 70° C.

Depending on the reaction conditions employed for oxidation of compounds of Formula VI either the 1-oxide or 1,1-dioxide derivative or a mixture of these is produced. The 1-oxide derivative can be directly oxidized to the 1,1-dioxide derivatives. Oxidation can be accomplished by employing various types of oxidizing agents including peracids such as hydrogen peroxide, performic acid, peracetic acid, perphthalic acid, perbenzoic acid and m-chloroperbenzoic acid; oxides of nitrogen such as dinitrogen tetroxide; nitric acid; and chromic compounds such as chromium trioxide and chromic acid-sulfuric acid (Jones' reagent).

When peracids are employed for the oxidation and the 1-oxide derivative is desired, it is preferred to use no more than one equivalent of the peracid. To prepare the 1,1-dioxide derivative at least two equivalents are theoretically required, but three or more equivalents can be used. Although the oxidations can be run in the absence of a solvent, the use of a solvent is preferred. Any solvent which is not itself oxidized can be used and solvents in the ester ketone, aliphatic and aromatic hydrocarbon and chlorinated hydrocarbon classes are commonly employed. The chlorinated aliphatic hydrocarbons are preferred. The reactions can be run at temperatures from about −5° C. to about 60° C. with the lower temperatures, e.g., from about 15° C., being preferred for the 1-oxide derivatives and the higher temperatures, e.g., from about 5° to about 50° C., being preferred for the 1,1-dioxide derivatives.

When an oxide of nitrogen such as $N_2O_4$ is employed, at least one equivalent is theoretically required for conversion to the 1-oxide derivative. With this type of oxidizing agent, oxidation to the 1,1-dioxide stage is more difficult and even with excesses of the dinitrogen tetroxide, the major product is the 1-oxide derivative. An inert solvent, for example, from the ester and chlorinated classes of solvents, is commonly employed although the reaction will proceed in the absence of a solvent. The reaction is usually run in the temperature range from about −5° C. to about 25° C. with from about 0° C. to about 15° C. being preferred. In some instances, the nitric acid salt of the 3-isothiazolone forms and this upon mild heating can be converted to the 1-oxide derivative.

When nitric acid is used as the oxidizing agent, the acid can have a concentration in the range from about 35 to about 70% with 65 to 70% being preferred. The reaction temperature can be from about −5° C. to about 35° C. with from about 0° C. to about 15° C. being preferred. The usual product is the 1-oxide derivative, which can be formed from the nitrate salt by mild heating in an aromatic hydrocarbon solvent e.g., in benzene.

When chromic acid is used as the oxidizing agent, it can be employed in from about 0.5 to about 2 or more equivalents. An inert solvent, such as ketonic solvent is commonly employed although oxidation will proceed in the absence of a solvent. The reaction is usually run at about room temperature, but will proceed at temperatures from about 0° C. to about 60° C. with from about 15° C. to about 35° C. being preferred.

The Diels-Alder reaction is well known in the art, however, its application to the reaction of compounds containing conjugated dienes with 3-isothiazolone-1-oxides and 1,1-dioxides is a novel adaptation of the reaction.

In general the Diels-Alder adducts of this invention are prepared by addition of a dienophile, the 3-isothiazolone 1-oxides and 1,1-dioxides, with a conjugated diene. The addition involves, in particular, the mixing of either equimolar amounts or slight excesses of either a 3-isothiazolone 1-oxide or 1,1-dioxide dienophile which is dissolved in an appropriate solvent with a diene of Formula II, III or IV which can be used either neat or dissolved in an appropriate solvent. The reaction mixture is then stirred from about one hour to about 24 hours at from about 20° C. to about 180° C. depending upon the solvent used and the reactants used. The reaction mixture can then either be cooled in an ice bath or stripped of its solvent and the product collected. The product can then be purified by appropriate means such as recrystallization, chromatography and the like or combinations thereof. The solvents which are appropriate for use in this addition reaction include any non-diene or non-dienophile solvents such as methylene chloride, chloroform, ethylene dichloride, nitrobenzene, dioxane and the like and mixtures thereof.

The following examples are presented as an illustration of some of the more preferred methods for preparing the adducts of this invention and are not to be construed in any way to be limitations of the breadth or scope of the present invention.

EXAMPLE I 5,6-Dimethyl-3a,4,7,7a-tetrahydro-1,2-benzisothiazol-3(2H)-one oxide To a solution of 2.2 g (0.02 mole) of 4-isothiazolin-3-one 1-oxide in 50 ml of ethylene dichloride is added 2.0 g (0.024 mole) of 2,3-dimethyl-1,3-butadiene. The mixture is stirred and maintained at 60° C. overnight. Concentration of the mixture yields a thick oil, which affords a white solid on trituration with hexane. The solid is filtered and air dried to yield 3.4 g (90%) or product, m.p. 135°-137° C. which can be recrystallized from ethyl acetate-hexane.

EXAMPLE II 5,6-Dimethyl-2-n-octyl-3a,4,7,7a-tetrahydro-1,2-benzisothiazol-3(2H)-one 1-oxide To a solution of 2.2 g (0.01 mole) of 2-n-octyl-4-isothiazolin-3-one 1-oxide in 15 ml of ethylene dichloride is added 1.1 g (0.012 mole) of 2,3-dimethyl-1,3-butadiene. The solution is stirred and maintained at 60° C. overnight. The mixture is concentrated to give a dark, thick oil. The oil is further purified by column chromatography (90% benzene, 10% acetone, silica) to yield 1.58 g (51%) of product as a yellow oil.

EXAMPLE IV 3a,4,7,7a-Tetrahydro-4,7-ethano-1,2-benzisothioazol-3(2H)-one 1,1-dioxide A 40 ml solution of ethylene dichloride containing 5.3 g (0.04 mole) of 4-isothiazolin-3-one 1,1-dioxide and 3.2 g (0.04 mole) of 1,3-cyclohexadiene is heated at reflux for 4 hours. The solution is cooled in an ice-water bath to give a white solid. The precipitate is filtered and air dried to yield 6.7 g (79.0%) of product, m.p. 200°-202° C., which can be recrystallized from ethyl acetate.

EXAMPLE V 5,6-Dimethyl-3a,4,7,7a-tetrahydro-1,2-benzisothiazol 3(2H) -one 1,1-dioxide A 40 ml solution of ethylene dichloride containing 5.3 g (0.04 mole) of 4-isothiazolin-3-one 1,1-dioxide and 3.3 g (0.04 mole) of 2,3-dimethyl-1,3-butadiene is heated at 45°-50° C. overnight. The golden solution is cooled and concentrated to give an oil. Trituration of the oil with ether gives a white solid, 7.7 g (80%), m.p. 110°-112° C., which can be recrystallized from ethyl acetate.

EXAMPLE IX

2-Methyl-3a,4,7,7a-tetrahydro-4,7-ethano-1,2-benzisothiazol 3(2H)-one 1-oxide

A 30 ml solution of ethylene dichloride containing 3.3 g (0.025 mole) of 2-methyl-4-isothiazolin-3-one 1-oxide and 2.0 g (0.025 mole) of cyclohexadiene is heated at 52°-53° C. and stirred overnight. The solution is concentrated to give 4.9 g (93%) of a white solid, m.p. 118°-120° C. which can be recrystallized from ethyl acetate.

EXAMPLE XIII 3a,7a-Dichloro-4,7-dihydro-methano-1,2-benzisothiazol-3(2H)-one A 40 ml solution of nitrobenzene containing 4.4 g (0.04 mole) of 4-isothiazolin-3-one 1-oxide and 10.9 g (0.04 mole) of hexachlorocyclopentadiene is heated at 120° C. for 4 hours. The nitrobenzene is removed by distillation to give a tarry material. Trituration of the tarry solid with ether gives 5.2 g (33.4%) of a brown solid. The brown solid is recrystallized from ether to give a white solid, m.p. >280° C.

EXAMPLE XIV 9,10[4',5']-Isothiazolaanthracene 12-oxide

An 80 ml solution of dioxane containing 8.8 g (0.08 mole) of 4-isothiazolin -3-one 1-oxide and 14.3 g (0.08 mole) of anthracene is heated to 105° C. This clear yellow solution is heated for 4 hours; a yellow solid is obtained on cooling. The yellow solid is triturated with ether and filtered to give 11.2 g of product, m.p. 259°-261° C., which can be recrystallized from ethyl acetate. Additional crops, 5.6 g and 5.3 g are obtained from the mother liquors (total yield 94%).

EXAMPLE XV

9-Methyl-9,10[4',5']-isothiazoloanthracene 12-oxide

An 80 ml solution of dioxane containing 4.4 g (0.04 mole) of 4-isothiazolin-3-one 1-oxide and 7.7 g (0.04 mole) of 9-methylanthracene is heated at reflux for 3 hours. The solution is cooled and concentrated to give a white solid. The solid is triturated with ether and collected to yield 7.8 g (63%) of product, m.p. 258°-260° C. which can be recrystallized from ethyl acetate.

EXAMPLE XVII

15-Chloro-13 methyl-9,10[4',5']-isothiazoloanthracene 12-oxide

To a solution of 4.95 g (0.03 mole) of 5-chloro-2-methyl-4-isothiazolin-3-one 1-oxide in 75 ml of nitrobenzene is added 5.88 g (0.033 mole) of anthracene. A catalytic quantity of aluminum chloride is added and the mixture is heated 130°-140° C. for 4 hours. After cooling to room temperature and standing overnight, the mixture is filtered to remove unreacted anthracene. The filtrate is evaporated under 0.05 mm pressure. The residue is dissolved in a minimum of ethyl acetate and treated with carbon (Darco G-60). On cooling, additional anthracene separates. Filtration, concentration and further cooling gives 2.8 g of crude product. Recrystallization from ethyl acetate gives four crops of material for a total of 2.2 g (21.3%) of product, m.p. 237.5°-239° C.

Table I $$\text{Structure with } R^4, R^5, R^3, X, R^2, R^5, (O)_n, N-R^1$$

| Example No. | $R^1$ | $R^2$ | $R^3$ | $R^4$ | $R^5$ | (X) | n |
|---|---|---|---|---|---|---|---|
| 1 | H | H | H | CH$_3$ | H | H, H | 1 |
| 2 | C$_8$H$_{17}$-n | H | H | CH$_3$ | H | H, H | 1 |
| 3 | H | H | H | H | H | C$_2$H$_4$ | 1 |
| 4 | H | H | H | H | H | C$_2$H$_4$ | 2 |
| 5 | H | H | H | CH$_3$ | H | H, H | 2 |
| 6 | C$_8$H$_{17}$-n | H | H | H | H | CH$_2$ | 1 |
| 7 | C$_8$H$_{17}$-n | H | H | H | H | C$_2$H$_4$ | 2 |
| 8 | C$_8$H$_{17}$-n | H | H | CH$_3$ | H | H, H | 2 |
| 9 | CH$_3$ | H | H | H | H | C$_2$H$_4$ | 1 |
| 10 | C$_4$H$_9$-n | H | H | H | H | C$_2$H$_4$ | 2 |
| 11 | C$_4$H$_9$-n | H | H | H | H | C$_2$H$_4$ | 1 |
| 12 | C$_8$H$_{17}$-n | H | H | H | H | C$_2$H$_4$ | 1 |
| 13 | H | H | H | Cl | Cl | CCl$_2$ | 1 |

Table II

| Example No. | $R^1$ | $R^2$ | $R^3$ | $R^4$ | n |
|---|---|---|---|---|---|
| 14 | H | H | H | H | 1 |
| 15 | H | H | H | CH$_3$ | 1 |
| 16 | H | H | H | H | 2 |
| 17 | CH$_3$ | Cl | H | H | 1 |

TABLE III

| Ex.-ample No. | mp°C. | Elemental Analysis Found/Calc'd | | | |
|---|---|---|---|---|---|
| | | C | H | N | S |
| 1 | 135–137 | 54.12(54.25) | 6.73(6.57) | 7.00(7.02) | 16.13(16.06) |
| 2 | oil | 65.12(65.55) | 9.44(9.38) | 4.20(4.49) | 10.18(10.29) |
| 3 | 183–185 | 54.31(54.80) | 5.78(5.62) | 6.95(7.12) | 16.16(16.25) |
| 4 | 200–202 | 50.84(50.67) | 5.40(5.19) | 6.52(6.56) | 14.96(15.04) |
| 5 | 110–112 | 50.24(50.22) | 6.11(6.08) | 6.37(6.50) | 14.76(14.89) |
| 6 | oil | 63.91(65.00) | 8.70(8.54) | 4.45(4.75) | 10.48(10.78) |
| 7 | 96–98 | 62.50(62.74) | 8.21(8.36) | 4.08(4.30) | 9.67(9.85) |
| 8 | oil | 60.83(62.35) | 8.64(8.92) | 4.16(4.27) | 10.09(9.79) |
| 9 | 119 | 56.86(56.85) | 6.28(6.20) | 6.62(6.62) | 15.19(15.17) |
| 10 | 123–125 | 57.68(57.97) | 7.01(7.10) | 5.11(5.19) | 11.99(11.90) |
| 11 | 45–47 | 60.94(61.63) | 7.34(7.55) | 5.49(5.52) | 12.54(12.65) |
| 12 | oil | 66.21(65.98) | 8.68(8.79) | 4.59(4.52) | 10.28(10.36) |
| 13 | 280 | 24.93(24.64) | 0.98(0.77) | 3.53(3.59) | 8.32(8.22) |
| 14 | 259–261 | 68.91(69.40) | 4.59(4.40) | 4.76(4.75) | 10.81(10.85) |
| 15 | 258–260 | 69.99(69.88) | 5.00(4.89) | 4.34(4.53) | 10.31(10.36) |
| 16 | 268–270 | 65.78(65.58) | 4.34(4.20) | 4.39(4.49) | 10.48(10.29) |
| 17 | 237–239 | 63.20(62.88) | 4.23(4.08) | 3.96(4.08) | 9.53(9.32) |

The Diels-Alder adducts of 3-isothiozolone 1-oxides and 1,1-dioxides of this invention can be readily utilized as slimicides, algaecides, bactericides, and fungicides in any locus and particularly in aqueous media, such as, for example, water-cooling systems, swimming pools, paper pulp processes, aqueous polymer dispersions, water-based paints, and the like. In addition, these compounds and compositions containing them can function as, for example, fabric and leather preservatives, cosmetic preservatives, soap additives, sanitizing agents, such as in laundry soaps and detergents, preservatives for metal working compounds, such as emulsifiable cutting oils, preservatives for fuels, fiber spin finish biocides, and the like.

These adducts are also useful as laundry sanitizing agents, in which fast speed-of-kill is particularly advantageous. Generally, about 0.01 to about 10% by weight and preferably about 0.05 to about 5% by weight, of the adduct will be added to a soap detergent to make a sanitizing laundry composition. These adducts can also be added directly to the laundry wash water, generally at a concentration of about 0.5 to about 1000 parts per millions by weight. The adducts of this invention are also useful as postemergence herbicides on monocotyledons and dicotyledons. For use as herbicides the compounds may be applied at a rate of 0.25 to 50 pounds of the active ingredient per acre and preferably in the range of 1 to 15 pounds per acre.

In general, a locus subject to contamination by microorganisms can be protected in accordance with this invention by incorporating into the locus the Diels-Alder adduct of 3-isothiazolone 1-oxides and 1,1-dioxides in an amount which is effective to control the microorganisms. The term "contamination" is meant to include attack by microorganisms which leads to a chemical or physical breakdown or disintegration of the locus as well as proliferation of the microorganisms within the locus without an accompanying deleterious effect. The exact amount or adduct required will, of course, vary with the medium being protected, the microorganisms being controlled, the particular adduct or compositions containing the adduct being employed, the degree of control desired, and other factors. Typically, in a liquid medium suitable control is obtained when the adducts are incorporated in the range of from about 0.1 to about 10,000 parts per million (PPM) or from about 0.00001 to about 1% based on the weight of the medium. A range of about 1 to about 2000 ppm is preferred.

The term "control" as employed in the specification and claims of this application is to be construed as the effect of any means which adversely affects the existence or growth of any living organism or microorganism. This effect may comprise complete killing action, eradication, arresting in growth, inhibition, reduction in number or any combination of these effects.

The adducts of the invention are also useful as paint preservatives and paint fungistats. Microbial activity in water-based and oil-based paint emulsions is inhibited when the active ingredients are incorporated into the paint. The adducts are also mildewcides for paint films when incorporated in paint formulations.

The Diels-Alder adducts of 3-isothiazolone 1-oxides and 1,1-dioxides of this invention are especially useful as agricultural bactericides and fungicides. As such as they are particularly valuable when formulated in bactericidal and fungicidal compositions. Such compositions normally comprise an agronomically acceptable carrier and a 3-isothiazolone 1-oxide or 1,1-dioxide adduct or mixtures of the two as the active agent. When necessary or desirable, surfactants or other additives can be incorporated to give uniformly formulated mixtures. By "agronomically acceptable carrier" is meant any substance which can be utilized to dissolve, dispense, or diffuse the chemical incorporated therein without impairing the effectiveness of the toxic agent and which does no permanent damage to the environment, soil, equipment or agronomic crops.

For use as pesticides, the compounds of this invention are usually taken up in an agronomically acceptable carrier or formulated so as to render them suitable for subsequent dissemination. For example, the adducts can be formulated as wettable powders, emulsion concentrates, dusts, granular formulations, aerosols or flowable emulsifiable concentrates. In such formulations, the adducts are extended with a liquid or solid carrier and, when desired, suitable surfactants are incorporated.

The adducts of this invention can be dissolved in a water-miscible liquid, such as methanol, ethanol, isopropanol, acetone, and the like or mixtures thereof. Such solutions are easily extended with water.

The 3-isothiazolone 1-oxide or 1,1-dioxide adducts can be taken up on or mixed with a finely particled solid carrier, as for example, clays, inorganic silicates, carbonates, and silicas. Organic carriers can also be employed. Dust concentrates are commonly made wherein the adducts are present in the range of from about 20 to about 80%. For ultimate applications these concentrates are normally extended with additional solid from about 1 to about 20%.

Wettable powder formulations are made by incorporating the adducts of this invention in an inert, finely divided solid carrier along with a surfactant which may be one or more emulsifying, wetting, dispersing or spreading agents or blends of these. The adducts are usually present in the range of from about 10 to about 80% by weight and the surfactants in from about 0.5 to about 10% by weight. Commonly used emulsifying and wetting agents include polyoxyethylated derivatives of alkylphenols, fatty alcohols, fatty acids and alkylamines, alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenapthalene sulfonates.

One convenient method for preparing a solid formulation is to impregnate the toxicant onto the solid carrier by means of a volatile solvent, such as acetone. In this manner adjuvants such as activators, adhesives, plant nutrients, synergists and various surfactants, can also be incorporated.

Emulsifiable concentrate formulations can be prepared by dissolving the Diels-Alder adduct of 3-isothiazolone 1-oxides or 1,1-dioxides of this invention in an agronomically acceptable organic solvent and adding a solvent-soluble emulsifying agent. Suitable solvents are usually water-immiscible and can be found in the hydrogen, chlorinated hydrocarbon, ketone, ester, alcohol and amide classes of organic solvents. Mixtures of solvents are commonly employed. The surfactants useful as emulsifying agents can constitute from about 0.5 to about 10% by weight of the emulsifiable concentrate and can be anionic, cationic or non-ionic in character. Anionic surfactants include alcohol sulfates or sulfonates, alkylarene sulfonates and sulfosuccinates. Cationic surfactants include fatty acid alkylamine salts and fatty acid alkyl quaternaries. Non-ionic emulsifying agents include alkylene oxide adducts or alkylphenols, fatty alcohols, mercaptans and fatty acids. The concentration of the active ingredients may vary from about 10 to about 80%, preferably in the range of about 25 to about 50%.

For use as phytopathogenic agents, these compounds should be applied in an effective amount sufficient to exert the desired biocidal activity by techniques well known in the art. Usually, this will involve the application of the active ingredient to the locus to be protected in an effective amount when incorporated in an agronomically acceptable carrier. However, in certain situations, it may be desirable and advantageous to apply the adducts directly into the locus to be protected without the benefit of any substantial amount of carrier. This is a particularly effective method when the physical nature of the 3-isothiazolone 1-oxide or 1,1-dioxide adduct is such as to permit what is known as "low volume" application, that is, when the adducts are in liquid form or substantially soluble in higher boiling solvents.

The application rate will, of course, vary depending upon the purpose for such application, the adducts being utilized, the frequency of dissemination and the like.

For use as agricultural bactericides and fungicides, dilute sprays can be applied at concentrations of from about 0.05 to about 20 pounds of the active ingredient per 100 gallons of spray. They are usually applied at from about 0.1 to about 10 pounds per 100 gallons and preferably at about 0.125 to about 5 pounds per 100 gallons. In more concentrated sprays, the active ingredient is increased by a factor of about 2 to 12. With dilute sprays, applications are usually made to the plants until run-off is achieved; whereas, with more concentrated or low-volume sprays, the materials are applied as mists.

The adducts of this invention may be utilized as the sole biocidal agents or they may be employed in conjunction with other fungicides, bactericides, algaecides, slimicides, insecticides, miticides, or with other comparable pesticides.

It is to be understood that changes and variations may be made without departing from the spirit and scope of the invention as defined by the appended claims.

We claim:

1. A compound of the formula

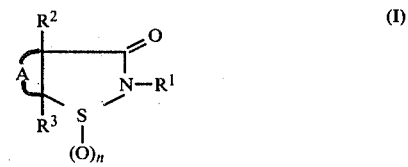

wherein $R^1$ is hydrogen; $(C_1-C_{18})$ alkyl; or $(C_1-C_{18})$ alkyl substituted with up to three substituents selected from the group consisting of hydroxyl, halogen, $(C_1-C_4)$ alkoxy, cyano and carboxy; $(C_3-C_{12})$ cycloalkyl, $(C_7-C_{11})$ aralkyl, or halogen, $(C_1-C_4)$ alkyl or $(C_1-C_4)$ alkoxy substituted aralkyl; $(C_6-C_{10})$ aryl or halogen, $(C_1-C_4)$ alkyl or nitro substituted aryl;

$R^2$ and $R^3$ are independently hydrogen, halogen or $(C_1-C_4)$ alkyl;

n is the integer 1 or 2; and A is a group of the formula

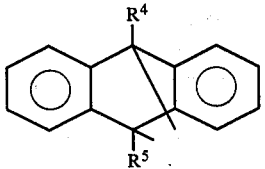

(II)

wherein
$R^4$ and $R^5$ are independently hydrogen, halogen, or $(C_1-C_4)$ alkyl; or the group

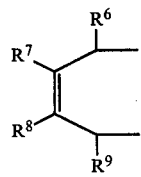

(III)

wherein
$R^6$, $R^7$, $R^8$ and $R^9$ are independently hydrogen, halogen or $(C_1-C_4)$ alkyl; or the group

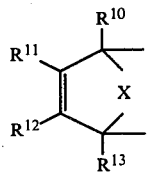

(IV)

wherein
$R^{10}$, $R^{11}$, $R^{12}$ and $R^{13}$ are independently hydrogen, halogen or $(C_1-C_4)$ alkyl;
X is oxygen, sulfur or $—(CY_2)_p—$
wherein
Y is hydrogen or halogen and p is 1 or 2.

2. A compound according to claim 1 wherein
$R^1$ is hydrogen or $(C_1-C_{18})$ alkyl;
$R^2$ and $R^3$ are independently hydrogen or halogen;
A is a group of Formula (II)
wherein
$R^4$ and $R^5$ are independently hydrogen or methyl; or
A is a group of Formula (III)
wherein
$R^6$, $R^7$, $R^8$ and $R^9$ are independently hydrogen or methyl; or
A is a group of Formula (IV)
wherein
$R^{10}$, $R^{11}$, $R^{12}$ and $R^{13}$ are hydrogen, halogen or methyl
X is oxygen, sulfur or $—(CY_2)_p—$
wherein
Y is hydrogen or chlorine and p is 1 or 2.

3. A compound according to claim 1 wherein
$R^1$ is hydrogen or $(C_1—C_8)$ alkyl;
$R^2$ and $R^3$ are hydrogen or chlorine;
A is a group of Formula (II)
wherein
$R^4$ and $R^5$ are hydrogen; or
A is a group of Formula (III)
wherein
$R^6$, $R^7$, $R^8$ and $R^9$ are hydrogen; or
A is a group of Formula (IV)
wherein
$R^{10}$, $R^{11}$, $R^{12}$ and $R^{13}$ are hydrogen or chlorine and
X is $—(CY_2)_p—$
wherein
Y is hydrogen and p is 1 or 2.

4. A compound according to claim 3 wherein A is the group of Formula (II).

5. A compound according to claim 3 wherein A is the group of Formula (III).

6. A compound according to claim 3 wherein A is the group of Formula (IV).

7. A method for controlling phytopathogenic fungi which comprises applying to a plant, to plant seeds or to the plant habitat a fungicidally effective amount of a compound of claim 1.

8. A method according to claim 7 wherein the effective amount of the compound is from 0.1 to 25 lbs. per acre.

9. A fungicidal composition for controlling phytopathogenic fungi which comprises an agronomically acceptable carrier and, as the active ingredient a fungicidally effective amount of a compound of claim 1.

* * * * *